United States Patent
Baselli et al.

(10) Patent No.: US 10,358,347 B1
(45) Date of Patent: Jul. 23, 2019

(54) PORTABLE CHLORINE DIOXIDE GENERATOR

(71) Applicants: Juan Carlos Baselli, Los Angeles, CA (US); Spencer Blua, Torrance, CA (US)

(72) Inventors: Juan Carlos Baselli, Los Angeles, CA (US); Spencer Blua, Torrance, CA (US)

(*) Notice: Subject to any disclaimer, the term of this patent is extended or adjusted under 35 U.S.C. 154(b) by 0 days.

(21) Appl. No.: 15/634,101

(22) Filed: Jun. 27, 2017

Related U.S. Application Data

(63) Continuation of application No. 15/092,887, filed on Apr. 7, 2016, now Pat. No. 9,718,686, which is a continuation of application No. 13/875,736, filed on May 2, 2013, now Pat. No. 9,333,475, which is a continuation of application No. 13/684,638, filed on Nov. 26, 2012, now abandoned.

(60) Provisional application No. 61/563,723, filed on Nov. 25, 2011.

(51) Int. Cl.
| | |
|---|---|
| *B65B 7/02* | (2006.01) |
| *C01B 11/02* | (2006.01) |
| *A61L 2/20* | (2006.01) |
| *A61L 2/26* | (2006.01) |
| *B65B 7/28* | (2006.01) |
| *B65B 61/20* | (2006.01) |
| *B65B 51/10* | (2006.01) |

(52) U.S. Cl.
CPC .............. *C01B 11/024* (2013.01); *A61L 2/20* (2013.01); *A61L 2/26* (2013.01); *B65B 7/02* (2013.01); *B65B 7/28* (2013.01); *B65B 51/10* (2013.01); *B65B 61/20* (2013.01); *A61L 2202/11* (2013.01); *A61L 2202/16* (2013.01)

(58) Field of Classification Search
None
See application file for complete search history.

(56) References Cited

U.S. PATENT DOCUMENTS

| | | |
|---|---|---|
| 4,051,229 A | 9/1977 | Isa et al. |
| 4,104,190 A | 8/1978 | Hartshorn |
| 4,250,144 A | 2/1981 | Ratigan |
| 4,421,730 A | 12/1983 | Isa et al. |
| 4,689,169 A | 8/1987 | Mason et al. |
| 5,126,070 A | 6/1992 | Leifheit et al. |
| 5,174,868 A | 12/1992 | Lipsztajn et al. |

(Continued)

*Primary Examiner* — Anita Nassiri-Motlagh
(74) *Attorney, Agent, or Firm* — Maier & Maier, PLLC

(57) ABSTRACT

The present invention provides a safe, disposable and biodegradable chlorine dioxide micro generator that uses water soluble paper and hydrogel or compressed cellulose encased in filter paper pouch. The chemicals are kept in a stabilize form until activated by the addition of water. Multiple levels of protection against early exposure to water such as a foil pouch and an impermeable outer container allow for the safe transportation and storage in small, ready for deployment amounts of the chemicals. Water permeated the chemical pack housing and dissolves the paper walls of the chemical pouch housing and then the water facilitates the reaction between the acid and the sodium chlorite to form chlorine dioxide gas as will be described further hereunder. Absorbent and permeable materials packaged around the chemicals provide for the safe containment of the chlorine dioxide solution, and the expeditious aeration and release of the chlorine dioxide gas, once the chemical reaction has been completed.

20 Claims, 3 Drawing Sheets

(56) References Cited

U.S. PATENT DOCUMENTS

| | | |
|---|---|---|
| 5,306,440 A | 4/1994 | Ripley et al. |
| 5,366,714 A | 11/1994 | Bigauskas |
| 5,407,656 A | 4/1995 | Roozdar |
| 5,797,244 A | 8/1998 | Nippes et al. |
| 5,965,264 A | 10/1999 | Barenbery et al. |
| 6,171,558 B1 | 1/2001 | Simpson |
| 6,431,279 B1 | 8/2002 | Zaid et al. |
| 6,602,442 B1 | 8/2003 | Pitochelli |
| 6,605,304 B1 | 8/2003 | Wellinghoff et al. |
| 6,607,696 B1 | 8/2003 | Hamilton et al. |
| 6,881,320 B1 | 4/2005 | Krafton et al. |
| 7,150,854 B2 | 12/2006 | Koermer et al. |
| 7,160,484 B2 | 1/2007 | Thangaraj |
| 7,383,946 B2 | 6/2008 | Hughes |
| 7,534,398 B2 | 5/2009 | Dee et al. |
| 7,695,692 B2 | 4/2010 | Sanderson |
| 2004/0241065 A1 | 12/2004 | Kampa |
| 2005/0079122 A1 | 4/2005 | DiMascio |
| 2005/0224750 A1 | 10/2005 | Yang et al. |
| 2006/0034750 A1 | 2/2006 | Lee et al. |
| 2006/0051285 A1 | 3/2006 | Hawker |
| 2006/0120945 A1 | 6/2006 | Warner |
| 2006/0280673 A1 | 12/2006 | DiMascio |
| 2008/0152580 A1 | 6/2008 | Simpson |
| 2008/0241276 A1 | 10/2008 | Willey et al. |
| 2008/0292534 A1 | 11/2008 | Richardson et al. |
| 2009/0008238 A1 | 1/2009 | Williams |
| 2010/0189631 A1 | 7/2010 | Noszticzius et al. |
| 2011/0000860 A1 | 1/2011 | Bland et al. |
| 2011/0020472 A1 | 1/2011 | Coughlin |

PORTABLE CHLORINE DIOXIDE GENERATOR

CROSS-REFERENCE TO RELATED APPLICATIONS

This application claims the benefit of U.S. Provisional Patent Application No. 61/563,723, filed on Nov. 25, 2011; U.S. patent application Ser. No. 13/684,638, filed on Nov. 26, 2012; U.S. patent application Ser. No. 13/875,736, filed on May 2, 2013; and U.S. patent application Ser. No. 15/092,887, filed on Apr. 7, 2016, each entitled "PORTABLE CHLORINE DIOXIDE GENERATOR," the entire contents of which are hereby incorporated by reference.

BACKGROUND

1. Field of the Invention

The present application relates to a disposable and biodegradable chlorine dioxide micro generator from portable, stable chemicals, using for example water soluble paper and hydrogel or compressed cellulose encased in a filter paper pouch.

2. Description of the Prior Art

Chlorine Dioxide (herein also referred to by "ClO2" or "ClO2") is a known biocide and disinfectant. It works by oxidizing single cell organisms in a known manner to kill the organism. Chlorine dioxide is currently used in commercial buildings to disinfect and deodorize various rooms and other enclosed areas. It has been known to be used in gymnasiums and other sports facilities to prevent staph infections while simultaneously deodorizing the facility. However, ClO2 is an unstable chemical that breaks down especially in ultraviolet light and must be generated on site by large, bulky industrial equipment making it inaccessible to smaller sites at a reasonable cost.

Because of the inherent instability of chlorine dioxide, it is currently generated as needed. This is typically done by mixing a small amount of sodium chlorite and acids from large canister reservoirs. The sodium chlorite is mixed with the acid, such as for example, Citric acid, sodium bisulfate, hydrochloric acid, etc. in large, industrial machinery. The separate canisters prevent unintended or premature mixing of the chemicals, but require porting around excess equipment to the desired site. It is therefore desired to provide a portable chlorine dioxide generator that can deploy small amounts of chlorine dioxide gas, while ensuring that the gas generation does not occur before the point of deployment. While the chlorine dioxide is not poisonous, it is at a minimum unpleasant or unhealthy to breathe, analogous to many household cleaners and thus premature mixing or "leakage" could have unwanted or deleterious consequences.

SUMMARY

The present invention provides a safe, disposable and biodegradable chlorine dioxide micro generator that uses exposure to water to trigger a reaction between small quantities of provided chemicals, such as sodium chlorite and an acid to produce the chlorine dioxide. In one embodiment, water soluble paper and hydrogel or compressed cellulose encased in a filter paper pouch surround the chemicals and allow water to permeate to the chemicals at the time of generation. The chemicals are kept in a dry, stabilized form until activated by the addition of water by multiple levels of protection. These levels include desiccants, physical separation, stabilizers, and impermeable barriers. These levels protect against early exposure to water to allow for the safe storage and transportation of the chemicals in small, pre-measured amounts of the chemicals suitable for the intended application site.

Accordingly, it is a principal object of a preferred embodiment of the invention to provide a one time, single use chlorine dioxide generator that is safe to use, stable during storage and shipment, and is readily deployable.

It is another object of the invention to provide a stable environment for the sodium chlorite and acids to exist in a single package without prematurely forming chlorine dioxide.

It is a further object of the invention to provide packaging for the chemicals that in the absence of water acts to separate the chemicals, and during introduction of water to the packaging facilitates a reaction between the enclosed chemicals to form chlorine dioxide.

Still another object of the invention is to provide in at least one embodiment separate compartments for the chemicals to further forestall a premature or unintended reaction between the chemicals.

It is yet another object of the invention according to at least one embodiment to provide cellulose material to absorb and contain the liquid ClO2 solution and expedites the aeration of said solution for a more efficient and rapid release of ClO2 gas from the system.

It is an object of the invention to provide improved elements and arrangements thereof in an apparatus for the purposes described which is inexpensive, dependable and fully effective in accomplishing its intended purposes.

These and other objects of the present invention will be readily apparent upon review of the following detailed description of the invention and the accompanying drawings. These objects of the present invention are not exhaustive and are not to be construed as limiting the scope of the claimed invention. Further, it must be understood that no one embodiment of the present invention need include all of the aforementioned objects of the present invention. Rather, a given embodiment may include one or none of the aforementioned objects. Accordingly, these objects are not to be used to limit the scope of the claims of the present invention.

BRIEF DESCRIPTION OF THE DRAWINGS

Similar reference characters denote corresponding features consistently throughout the attached drawings.

DETAILED DESCRIPTION OF THE PREFERRED EMBODIMENT(S)

The present invention is to a single use, compact chlorine dioxide generator. As best shown with reference to the drawings, the system and method for generating chlorine dioxide is shown.

Figure 1:
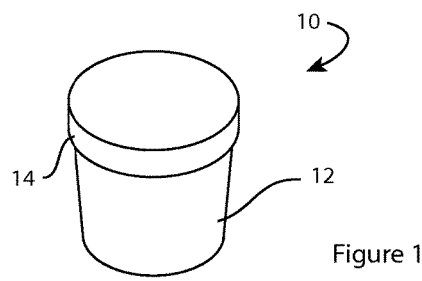
FIG. 1 is an environmental perspective view of a container housing the components of the system.
Figure 2:
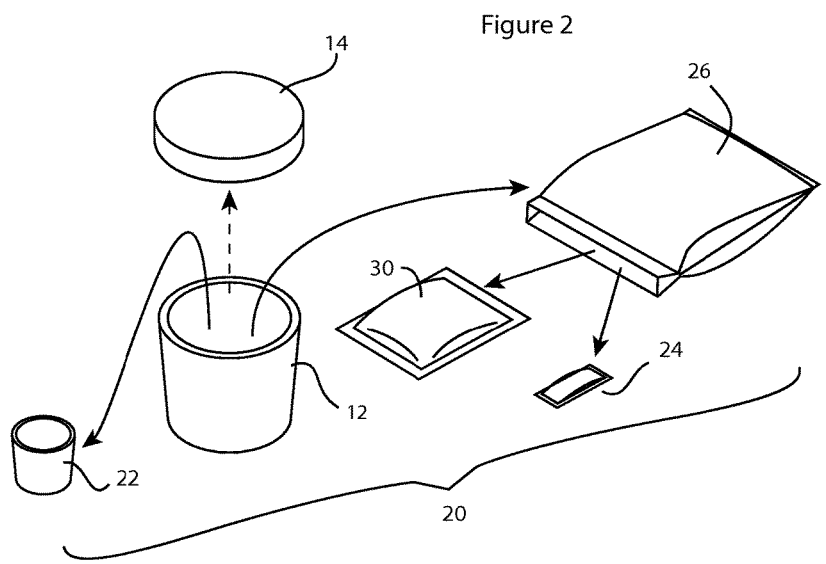
FIG. 2 is an exploded view of the components of the system.

The system includes a container 10 (FIG. 1) having a lower cup portion 12 and lid 14 for containing all of the parts of the system and for preventing the introduction of any moisture to the system. As shown in FIG. 2, removal of the lid 14 from the cup 12 allows access to and removal of the optional components of the system 20. Within the cup 12 are initially contained a water measuring cup 22, and a foil pouch 26 containing a chemical pack housing 30 and a desiccant pack 24.

In general, the materials are removed from the cup and the chemical pack housing 30 is removed from the foil pouch 26. A measured amount of water and the chemical pack housing are placed in the cup in the proper orientation, preferably with the chemical pack placed in the cup prior to the water. The water eventually is brought into contact with the chemicals within the chemical pouch 40 and facilitates the reaction between the acid and the sodium chlorite to form chlorine dioxide as will be described further hereunder.

The Components

The cup 12 and lid 14 that comprise the container are preferably made of an impermeable material, such as paper, plastic, etc. In the most preferred form, the cup is made from an impermeable paper so that the elements of the system may readily be recycled or biodegraded. The container may be an important layer in preventing premature introduction of any water to the chemicals, but in some circumstances may be optional.

A foil pouch 26 is provided to house the chemical pack housing 30 during storage and shipment and is used to redundantly protect the chemicals from the premature introduction of moisture or liquids to the chemicals to prevent an unintended reaction of the chemicals with each other. Foil or other impermeable materials can be used on the walls of the pouch 26 to prevent moisture in or out of the pouch.

A desiccant 24 is provided within the foil pouch 26 to prevent moisture from accumulating within the foil pouch 26 during shipping and storage. One skilled in the art would understand that the use of a desiccant is well known for lowering the humidity of a closed compartment and that its use or an alternative humidity lowering device is not necessary for the operation of the invention, but is merely provided to maintain a stable environment. The heart of the system, however, is the chemical pack 30 housing the chemical pouch 40 with the active ingredients necessary for generating chlorine dioxide.

Chemical Pack Construction

The chemical pack housing 30 may have many configurations, several of which are described herein. The configuration used in a particular system 20 may vary based on the measure of chemicals used in order to achieve different levels of ClO2 concentrations and with the size of the confined environment to be treated.

Figure 3:
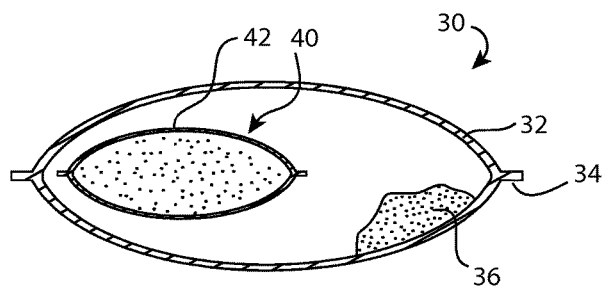
FIG. 3 is a break-away view of the chemical pouch and outer housing according to at least a first embodiment of the invention.

With reference to FIG. 3, the chemical pack housing 30 has an outer filter paper (or other porous or mesh material) wall 32, preferably joined together along a seam 34 joining the halves of the filter paper wall 32 together. Alternatively, any paper wall of the system 20 could also use other materials other than water soluble paper. For example water soluble film could be used, or even non-dissolvable filtration material could be used as long as water penetrates to allow the desired reaction to occur.

Within the filter paper outer wall 32, the chemical pack housing 30 is stuffed with an absorbent material such as hydro gel or compressed cellulose 36 or other open cell foam/material, which may be synthetic or organic, preferably having a high gas aeration capability. More preferably the cellulose takes the form of sponge particles 36 as will be described further hereunder. The absorbent material 38 serves several functions. First it absorbs the liquid ClO2 generated by the chemical reactions so as to safely contain said solution to avoid any spillage that could cause damage to the surroundings. And in operation, the absorbent material 36 facilitates and expedites the aeration and release of ClO2 gas into the atmosphere.

In a preferred embodiment, the cellulose material of the chemical pack housing 30 is comprised of a number of smaller cellulose blocks 36. Each block may be made of a dehydrated, compressed natural sponge or other cellulose source. By cutting a compressed sponge into approximately $2/16"$ by $2/16"$ cubes, it has been found that the capillary properties of the sponge increases to optimum levels to absorb liquid ClO2 rapidly, while allowing for sufficient pathways for the gas created in the chemical reaction to aerate and escape between the cellulose cubes better than a single layer or layers of cellulose material.

The chemical pouch 40 according to at least one preferred embodiment contains both the sodium chlorite and the activating acid in a single structure. To prevent contact and/or an unintended reaction between the chemicals, a stabilizer is provided with and between the chemicals to forestall reaction. A preferred stabilizer is talcum powder ("talc"), but other stabilizers could also be used such as calcium chloride. One reason that the talcum powder may work well as a stabilizer is that it coats the granular surfaces of the chemicals to create a physical boundary between the chemicals. The talcum powder may also lower humidity reaching the chemicals to further prevent an unintended, premature reaction between the chemicals.

The stabilizer allows both of the chemicals to be safely stored within the same compartment. Housing both of the chemicals within the same housing has the benefit that once water is introduced to initiate chemical reaction, the acid and sodium chlorite are in close contact encouraging a full and complete reaction with low barriers to the escaping chlorine dioxide gas. The stabilizer also has the added advantage of providing a long shelf life for the product in the range of two years, well beyond what would be expected for this type of chlorine dioxide generator.

Figure 4:
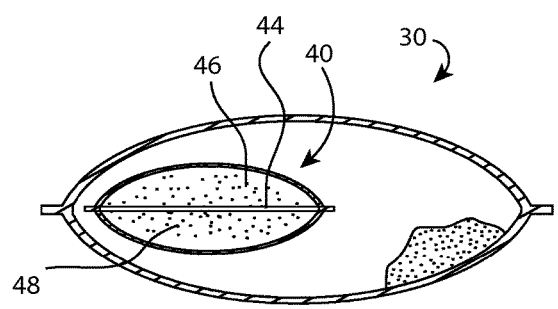
FIG. 4 is a break-away view of the chemical pouch and outer housing according to at least a second embodiment of the invention.

Depending on the size/amount of the chemicals and the intended environment that the chemicals will be used in, it may be desirable to store the chemicals in separate compartments to further ensure the chemicals cannot come in contact with each other prior to deployment at the intended site. As shown in FIG. 4, an additional paper barrier 44 can be introduced between the chemicals to keep the chemicals further separated. In this embodiment, it is preferred that the acid, such as citric acid be stored in the top compartment 46 and the sodium chlorite in the bottom compartment 48. Instructions or indicia on the chemical pouch 40 and/or the chemical pack housing 30 may be provided to ensure that the chemicals are deployed in the proper orientation. Having the acids on top of the sodium chlorite as the paper barrier dissolves during introduction of water to the system will ensure the most robust reaction between the acid and the sodium chlorite.

Figure 5:
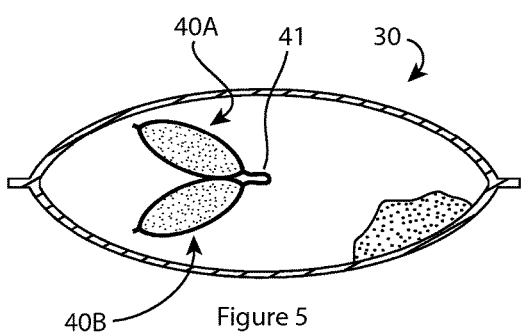
FIG. 5 is a break-away view of the chemical pouch and outer housing according to at least a third embodiment of the invention.

Another embodiment is shown in FIG. 5 having two separate pouches, one pouch 40A for the acid and a pouch 40B for the sodium chlorite. The chemicals pouch may be secured in close proximity by a tether 41 linking the pouches 40A & 40B. While shown in loose configuration in the figure, it may more practical to secure the pouches to each other at one or more point such that they maintain proper contiguous or close orientation to each other.

The chemical pack housing 30 itself may be fabricated with an outer pack wall 32 formed from filter paper filled with a measured amount of hydro gel (water absorbing polymer) or compressed cellulose 36. The process of fabrication is preferably performed in a room with less than 35% humidity and chemicals holding less than 1% humidity, filing the chemical pouch 40 with compound made with 80% technical grade sodium chlorite, organic acid (i.e., Citric acid, sodium bisulfate, etc.) and a stabilizer, then heat sealing the chemical pouch walls 40 together. The chemical pouch 40 is then placed within outer pack ("chemical pack housing") 30 with polymer and heat sealing outer pouch wall 34. This is then placed in the foil pouch 26 along with desiccant 24, and the foil pouch is sealed to create a watertight housing. This foil pouch 26 is then placed with the other components in the water impermeable container 10, with lid 14 sealed over the cup portion 12 to provide a long shelf life container for generating chlorine dioxide at the desired time in a small quantity.

Operation of the System

Figure 6:
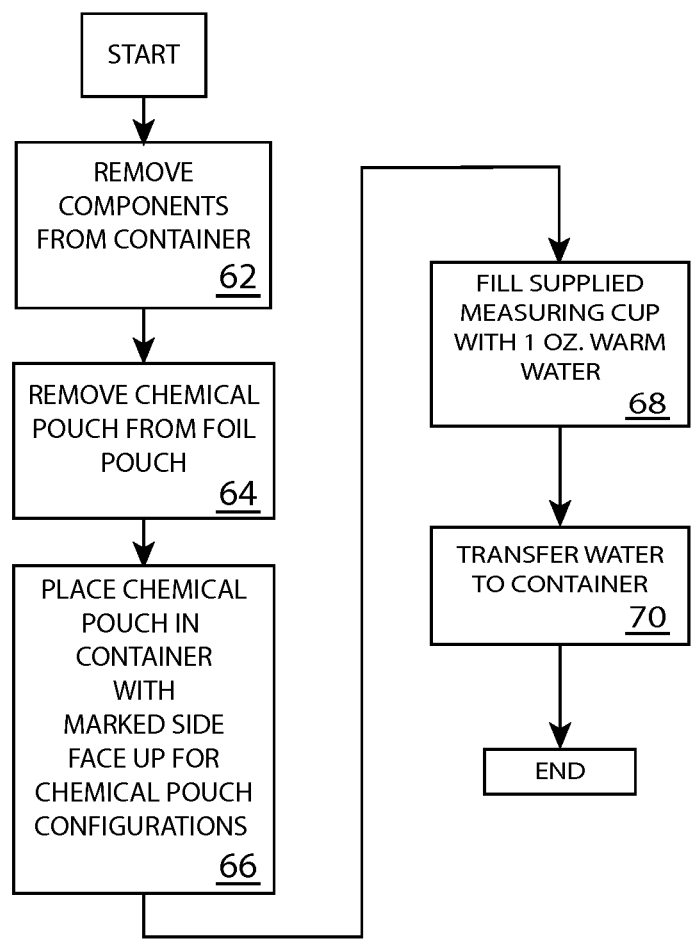
FIG. 6 is a flow diagram showing the steps for implementing the system.

In operation, as shown in the block diagram of FIG. 6, the self-contained chlorine dioxide generator is capable of creating the gas by the mere arrangement of the provided components plus the addition of a small amount of water. Referring to FIGS. 1, 2 and 6, operation of the system will be described.

To generate chlorine dioxide from the pre-packaged system, the lid 14 of the container 10 is separated from the cup portion 12. The components, namely, the measuring cup 22 and foil pouch 26 are removed 62 from the container cup portion 12 and set aside.

The proper orientation of the chemical pack housing 30 is then determined to maintain the chemical pouch within the pack housing in the proper position. The chemical pack housing 30 is then placed 66 in the cup in the desired orientation.

With the chemical pouch 40 properly placed in the cup 12, the measuring cup 22 is then filled 68 with the required amount of water (not shown) using indications on the cup or in accordance with instructions that may be provided. Once the proper amount of water is measured 68, it is poured 70 into the cup 12 on top of the chemical pouch 40 to initiate generation of the chlorine dioxide.

The water first passes through the outer filter paper pouch 32 of the chemical pack housing 30, allowing the water to come in contact and dissolve the soluble paper walls 42 of the chemical pouch 40 and initiates the chemical reaction by mixing all the chemicals together. The cellulose or hydro gel 36 aides in the reaction by facilitating the mixing of the chemicals caused by the expansion of the hydro gel or cellulose 36.

The outer paper walls 42 continue to dissolve in the water allowing for more water to reach the chemicals and stabilizer within the chemical pouch. Where the chemicals are stored in separate compartments (46, 48 FIG. 4) or separate pouches (40A, 40B FIG. 5), interposed walls break down in the water and allow the chemicals to react and proceed analogously to the single pouch embodiment.

When sufficient water has permeated into the chemicals to overcome the stabilizer, the acid and sodium chlorite can react with each other to form a chlorine dioxide gas. The gas then percolates out through the cellulose and through gaps in the outer chemical pack housing walls 32 that have dissolved. The gas continues to expand and flow out of the cup 12 into the enclosed environment around the cup. The chlorine dioxide gas oxidizes or otherwise eliminates single-celled organisms within the enclosed space around the cup, preferably killing any odor-causing organisms. After a short period of time, the chlorine dioxide then begins to break up into salts and water. Since only a small amount of gas per volume of room is required to neutralize the organisms, the amount of salt and water should be negligible and should not create a need for separate cleanup of the resulting byproducts. In this way, the self-contained chlorine dioxide generator generates sufficient gas to deodorize a confined space and breaks up easily into simple, environmentally friendly compounds. The articles left after the process, namely the chemical pack 30, and active ingredients as well as the paper cup can be recycled or biodegraded. And unlike the commercial gas generators, there is no industrial equipment or canisters left after the application of ClO2 at the site to haul away.

Slow Release System

An alternative to adding water to the cup is to merely deploy the system as the chemical pack housing 30 within the cup and allow the ambient humidity of the surrounding environment to slowly allow the gradual introduction of moisture to the chemicals. Eventually as the humidity level of the interior of the chemical pack 30 and later chemical pouch 40 rise to the level of the room, the chemicals will slowly react to the moisture carried by the air to the chemical pouch 40. The time that the humidity takes to reach the chemicals could be enhanced by scoring the walls of the chemical pack 30 or simply by removing the chemical pouch 40 from the chemical pack 30, however this is not desirable because the chemical pack 30 acts as a fuse to delay the introduction of water/humidity to the chemicals and this may be defeated by removing the chemical pouch 40 from the pack. Additionally, the chemical pack housing 30 acts a physical boundary between the chemicals and the user to further safeguard the user from the chemicals.

Water Suspended Chlorine Dioxide

A similar process could also be used to create chlorine dioxide suspended in water by introducing the chemical pack housing 30 to a larger volume of water. In such case, certain components of the system may be unnecessary, such as the cup 12 and measuring cup 22. The chemical pack could be provided within the foil pack, and deployment could be as simple as dropping the chemical pack 30 (when removed from the foil pack) into a large volume of water to initiate generation of the gas. If the volume of water is contained in a closed tank of water, the ClO2 will stay within the water for a longer period of time instead of being released from the water as a gas. A pump/sprayer on the tank could be used to spray ClO2 containing water on a desired spot to remove odor or to kill single cell organisms or other affected materials. Alternatively, the pouch could be dropped into an open volume of water, and a mop or similar device could be used to apply the ClO2 containing water.

The housing 30 could be provided within a webbing, netting or other housing configuration to prevent the housing from be introduced to downstream pumps, for example in a system that pumps the combined water and chlorine dioxide directly onto the desired areas. Additionally, individual components of the system can be made to be dissolvable or non-dissolvable as needed for various applications.

While this invention has been described as having a preferred design, it is understood that it is capable of further modifications, uses and/or adaptations of the invention following in general the principle of the invention and including such departures from the present disclosure as come within the known or customary practice in the art to which the invention pertains and as maybe applied to the central features hereinbefore set forth, and fall within the scope of the invention and the limits of the appended claims. It is therefore to be understood that the present invention is not limited to the sole embodiment described above, but encompasses any and all embodiments within the scope of the following claims.

What is claimed is:

1. A method for manufacturing a portable chlorine dioxide generator, comprising:
    filling at least one chemical pouch with at least sodium chlorite, an acid, and a stabilizer, the stabilizer provided as a buffer between the sodium chlorite and acid, the chemical pouch comprising a plurality of water-permeable outer walls;
    sealing the chemical pouch by sealing at least one water-permeable outer wall of the chemical pouch to at least one other water-permeable outer wall of the chemical pouch;
    placing the chemical pouch within a chemical pack outer housing and sealing the chemical pack outer housing; and
    placing the chemical pack outer housing within a foil pouch and sealing the foil pouch.

2. The method of claim 1, further comprising placing the foil pouch within a water-impermeable cup having a lid, and sealing the lid.

3. The method of claim 1, further comprising placing a desiccant within the foil pouch.

4. The method of claim 1, wherein the sodium chlorite and the acid are intermingled in the chemical pouch.

5. The method of claim 1, wherein the sodium chlorite and the acid are placed in separate pouches secured in close proximity to one another by a tether.

6. The method of claim 1, wherein the foil pouch is water-impermeable.

7. The method of claim 1, wherein the plurality of water-permeable outer walls of the chemical pouch are formed from dissolvable paper.

8. The method of claim 1, wherein the chemical pack further comprises a water absorbent and permeable material between at least one outer wall of the chemical pack and the chemical pouch.

9. The method of claim 7, wherein the water absorbent and permeable material comprises at least one of hydro gel and compressed cellulose.

10. The method of claim 7, wherein the water absorbent and permeable material is comprised of a number of blocks of water absorbent and permeable material.

11. The method of claim 7, wherein the water absorbent and permeable material is comprised of a plurality of compressed cellulose cubes.

12. The method of claim 2, further comprising placing a measuring cup within the cup.

13. The method of claim 2, wherein the cup comprises at least one of plastic or an impermeable paper.

14. The method of claim 1, wherein the method is performed in a room having less than 35% humidity.

15. The method of claim 1, wherein each of the sodium chlorite, the acid, and the stabilizer holds less than 1% humidity.

16. The method of claim 1, wherein the sodium chlorite comprises 80% technical grade sodium chlorite.

17. The method of claim 1, wherein the acid comprises at least one of citric acid or sodium bisulfate.

18. The method of claim 1, wherein the stabilizer is talcum powder.

19. The method of claim 1, wherein the chemical pouch is heat-sealed.

20. The method of claim 1, wherein the chemical pack outer housing is heat-sealed.

* * * * *